US00PP36976P2

(12) United States Plant Patent
Bacon et al.

(10) Patent No.: US PP36,976 P2
(45) Date of Patent: Sep. 23, 2025

(54) GRAPEVINE PLANT NAMED 'SUGRA66'

(50) Latin Name: *Vitis vinifera*
Varietal Denomination: SUGRA66

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/042,489

(22) Filed: Jan. 31, 2025

(30) Foreign Application Priority Data

Mar. 22, 2024 (PE) ..... 544-2024/DIN

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./156, 205
See application file for complete search history.

(56) References Cited

U.S. PATENT DOCUMENTS

PP21,664 P3 * 1/2011 Cain ..... A01H 6/88
Plt./308

* cited by examiner

*Primary Examiner* — Karen M Redden
(74) *Attorney, Agent, or Firm* — Knobbe, Martens, Olson & Bear, LLP

(57) ABSTRACT

The new variety of grapevine 'SUGRA66' is characterized by the production of a large-sized, dark red violet and obtuse ovate berry with a very early season ripening date. The berries of 'SUGRA66' are moderately firm and juicy.

1 Drawing Sheet

Latin name of the genus and species claimed: *Vitis vinifera.*

Variety denomination: 'SUGRA66'.

CROSS-REFERENCE TO RELATED APPLICATIONS

This application claims the benefit of Peruvian Application No. 544-2024/DIN, filed on Mar. 22, 2024, which is incorporated by reference herein in its entirety.

BACKGROUND AND SUMMARY

This application relates to the discovery and asexual propagation of a new and distinct variety of grapevine, 'SUGRA66', as herein described and illustrated. The new variety was first selected as breeder number 'GR963R' by Terry A. Bacon and Terrence J. Frett in Wasco, Kern County, California in July 2020. The variety was originated by controlled hybridization.

The new variety 'SUGRA66' is characterized by the production of a large-sized, dark red violet and obtuse ovate berry with a very early season ripening date. The berries of 'SUGRA66' are moderately firm and very juicy.

The seed parent is 'Sugrafiftyfive' (U.S. Plant Pat. No. 30,935) and the pollen parent is 'Sugrafiftythree' (U.S. Plant Pat. No. 29,768). The parent varieties were first crossed in April 2017. The date of first sowing was March 2018, and the date of first flowering was February 2019.

The new variety 'SUGRA66' was first asexually propagated in December 2020 in Wasco, Kern County, California, by Terry A. Bacon and Terrence J. Frett using cuttings and grafting.

The fruit of the new variety 'SUGRA66' has rudimentary seed traces like its seed parent 'Sugrafiftyfive' (U.S. Plant Pat. No. 30,935), but ripening of the berries of the new variety 'SUGRA66' begins earlier on June 29, compared to July 5 for 'Sugrafiftyfive'. Additionally, the new variety 'SUGRA66' has dark red violet berries compared to greyed purple berries for 'Sugrafiftyfive'.

The new variety 'SUGRA66' is similar to its pollen parent 'Sugrafiftythree' (U.S. Plant Pat. No. 29,768) in that berry ripening takes place on June 29 in both varieties, but the new variety 'SUGRA66' has dark red violet berries compared to dark red berries for 'Sugrafiftythree'. Additionally, the new variety 'SUGRA66' has an obtuse ovate berry shape with a cluster weight of 600 g compared to the broad elliptic berry shape and cluster weight of 700 g for 'Sugrafiftythree'.

The fruit of the new variety 'SUGRA66' has rudimentary seed traces like 'Flame Seedless' (unpatented), but the berry shape is obtuse ovate and the berry weight is 7.5 g for the new variety 'SUGRA66' compared to a broad elliptic berry shape and 4.8 g berry weight for 'Flame Seedless'.

The fruit of the new variety 'SUGRA66' has a berry weight of 7.5 g like 'IFG 68-175' (U.S. Plant Pat. No. 21,664), but the berry shape of 'SUGRA66' is obtuse ovate compared to a broad ellipsoid berry shape for 'IFG 68-175'. Additionally, the ripening time of the new variety 'SUGRA66' is June 29 compared to August 10 for 'IFG 68-175'.

The fruit of the new variety 'SUGRA66' has rudimentary seed traces like 'Sheegene-12' (U.S. Plant Pat. No. 20,252), but the berry color is dark red violet compared to a red berry color for 'Sheegene-12'. Further, the ripening time of the new variety 'SUGRA66' is June 29 compared to August 1 for 'Sheegene-12'.

The new variety 'SUGRA66' has been shown to maintain its distinguishing characteristics through successive asexual propagations by, for example, hardwood cuttings.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'SUGRA66'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2015.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA66' plants grown in the vicinity of Wasco, Kern County, California during 2022, and is believed to apply to plants of the variety grown under similar conditions of soil and climate elsewhere.

VINE

General: (Measurements taken on a three-year-old plant).

- *Vine size*.—Large. Height: Approximately 2.0 m. Width: Approximately 2.5 m.
- *Vigor*.—Medium-high.
- *Density of foliage*.—Dense.
- *Productivity*.—Very productive.
- *Crop load*.—Approximately 30 kg per vine after thinning.
- *Own root*.—Yes.
- *Training method*.—Typically spur pruned leaving about 40 2-bud spurs.
- *Resistance*.—Neither resistance nor susceptibility to particular diseases or pests has been observed in this variety.

Trunk:

- *Shape*.—Stocky.
- *Diameter*.—Approximately 4.2 cm (at 30 cm above the soil line).
- *Straps*.—Short.
- *Surface texture*.—Medium shaggy.
- *Inner and outer bark color*.—Inner bark about Medium Greyed-Orange 166C and weathering to about Dark Greyed-Green 197B in the outer bark.

SHOOTS

Young shoot:

- *Form of tip*.—Wide open.
- *Intensity of anthocyanin coloration of tip*.—Weak.
- *Density of prostrate hairs on tip*.—Medium.
- *Density of erect hairs on tip*.—Absent or very sparse.
- *Color*.—About Medium Green 141C and Light Green 141D.

Woody shoot (observations made in the middle third of shoot):

- *Attitude before tying*.—Semi-drooping.
- *Growth of axillary shoots*.—Medium, about 17 to 21 cm in length.
- *Internode length*.—Very short, approximately 55 mm.
- *Width at node*.—Approximately 7 mm.
- *Cross section*.—Circular.
- *Surface texture*.—Striate.
- *Main color*.—About Medium Greyed-Orange 166B.
- *Color of dorsal side of internode*.—About Medium Greyed-Orange 166B.
- *Color of ventral side of internode*.—About Medium Greyed-Orange 166B.
- *Color of dorsal side of node*.—About Medium Greyed-Orange 166B.
- *Color of ventral side of node*.—About Dark Greyed-Orange 166A and Medium Greyed-Orange 166B.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 2 mm.
- *Color*.—About Light Green 149A.
- *Form*.—Bifurcated.
- *Number of consecutive tendrils*.—Up to 2.
- *Length of tendril*.—Short, approximately 12 cm.

LEAVES

Young leaves:

- *Color of upper surface of first 4 distal unfolded leaves*.—About Medium Yellow-Green N144C.
- *Average intensity of anthocyanin coloration of six distal leaves prior to flowering*.—Absent or very slight.
- *Density of prostrate hairs between veins at lower surface of 4th distal unfolded leaf*.—Absent or very sparse.
- *Density of erect hairs between veins at lower surface of 4th distal unfolded leaf*.—Absent or very sparse.
- *Density of prostrate hairs on veins at lower surface of 4th distal unfolded leaf*.—Absent or very sparse.
- *Density of erect hairs on veins at lower surface of 4th distal unfolded leaf*.—Absent or very sparse.

Mature leaves (observations made in the middle third of shoot):

*Size*.—Medium.
*Average length*.—Approximately 8 cm.
*Average width*.—Approximately 11 cm.
*Shape of blade*.—Pentagonal.
*Number of lobes*.—Approximately 5.
*Mature leaf profile*.—Undulate.
*Blistering surface of blade upper surface*.—Absent or very weak.
*Leaf blade tip*.—In the plane of the leaf.
*Undulation of margin*.—Slightly undulating.
*Thickness*.—Average — typical of *Vitis vinifera* species.
*Overall shape of teeth*.—Mixture of both sides straight and both sides convex.
*Length of teeth*.—Short, ranging from about 3 mm to 6 mm, usually 4 mm.
*Ratio length/width of teeth*.—Very small, nearly 1:1.
*General shape of petiole sinus lobes*.—Half open.
*Tooth at petiole sinus*.—Absent.
*Petiole sinus limited by veins*.—Absent.
*Shape of upper lateral sinus lobes*.—Mostly open.
*Depth of upper lateral sinuses*.—Shallow, approximately 1 cm to 2 cm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Usually about Light Green 138B becoming about Medium Grey-Brown 199C.

Upper leaf surface:

*Color*.—About Dark Green 141B.
*Surface texture*.—Smooth.
*Surface appearance*.—Dull.
*Anthocyanin coloration of main veins*.—Absent or very sparse.

Lower leaf surface:

*Color*.—About Medium Green 135C.
*Surface texture*.—Smooth, dull.
*Surface appearance*.—Dull.
*Anthocyanin coloration of main veins*.—Absent or very low.

Petiole:

*Length of petiole*.—Approximately 5 cm.
*Diameter*.—Approximately 2 mm.
*Length of petiole compared to middle vein*.—Slightly shorter; 5 cm for the petiole compared to 8 cm for middle vein.
*Density of prostrate hairs on petiole*.—Absent.
*Density of erect hairs on petiole*.—Absent.
*Color*.—About Light Green 142B.

Buds:

*Shape*.—Conical.
*Size*.—Medium, approximately 3 mm wide × 3 mm long.
*Position*.—Slightly held out.
*Bud fruitfulness*.—Basal, mostly fruitful.
*Time of bud burst*.—Very Early, approximately March 2nd for the southern San Joaquin Valley region of California.

FLOWERS

General:

*Flower type*.—Fully developed stamen and fully developed gynoecium.
*Position of first flowering node*.—Usually 5th node of current season growth.
*Number of inflorescences per shoot*.—Usually 1 cluster per shoot.
*Time of full bloom*.—Approximately May 10th in the southern San Joaquin Valley region of California.

FRUIT

General:

*Ripening period*.—Very early season, beginning about June 29th in the southern San Joaquin Valley region of California.
*Use*.—Fresh market.
*Storage quality*.—Good.

Cluster:

*Form*.—Short conical.
*Cluster size* (*peduncle excluded*).—Medium.
*Cluster length* (*peduncle excluded*).—Approximately 17 cm.
*Cluster width*.—Approximately 17 cm.
*Cluster weight*.—Approximately 600 g.
*Cluster density*.—Medium, loose-full.
*Number of berries*.—Approximately 90 berries after tipping.

Peduncle:

*Length*.—Long, approximately 7 cm.
*Diameter*.—Approximately 6 mm.
*Lignification of peduncle*.—Weak.
*Color*.—About Medium Yellow-Green 144A.

Berry:

*Size*.—Large, approximately 7.5 g.
*Dimensions*.—Width: Approximately 22 mm. Length: Approximately 25 mm.
*Uniformity of size*.—Somewhat uniform.
*Shape*.—Obtuse ovoid.
*Cross section*.—Circular.
*Skin color* (*without bloom*).—About Dark Violet Blue N92A and Dark Violet Blue N92C.
*Flesh color*.—About Medium Green 139C at full ripeness. About Medium Red-Purple 59C anthocyanin develops as it becomes past ripe.
*Anthocyanin color of flesh*.—Absent or very weak.
*Bloom* (*cuticular wax*).—Medium, typical of most commercial *Vitis vinifera*.
*Pedicel length*.—Approximately 11 mm.
*Pedicel thickness*.—Thin, approximately 1.5 mm.
*Berry separation from pedicel*.—Moderately easy.
*Seed traces*.—Rudimentary.
*Berry firmness*.—Moderately firm.
*Flesh juiciness*.—Juicy.
*Flesh texture*.—Moderately firm.
*Particular flavor*.—None.
*Refractometer test*.—About 17 Brix.
*Juice pH*.—About 3.78.

*Titratable acidity*.—About 0.64%.

*Brix:acid ratio*.—Approximately 26.5.

Skin:

*Skin thickness*.—Medium, about 175 μm.

*Skin texture*.—Smooth.

*Skin reticulation*.—Absent.

*Skin tenacity*.—Tenacious to flesh.

*Skin tendency to crack*.—Present.

*Skin sensitivity to sunburn*.—None.

What is claimed is:

1. A new and distinct variety of grapevine plant named 'SUGRA66', substantially as illustrated and described herein.

* * * * *

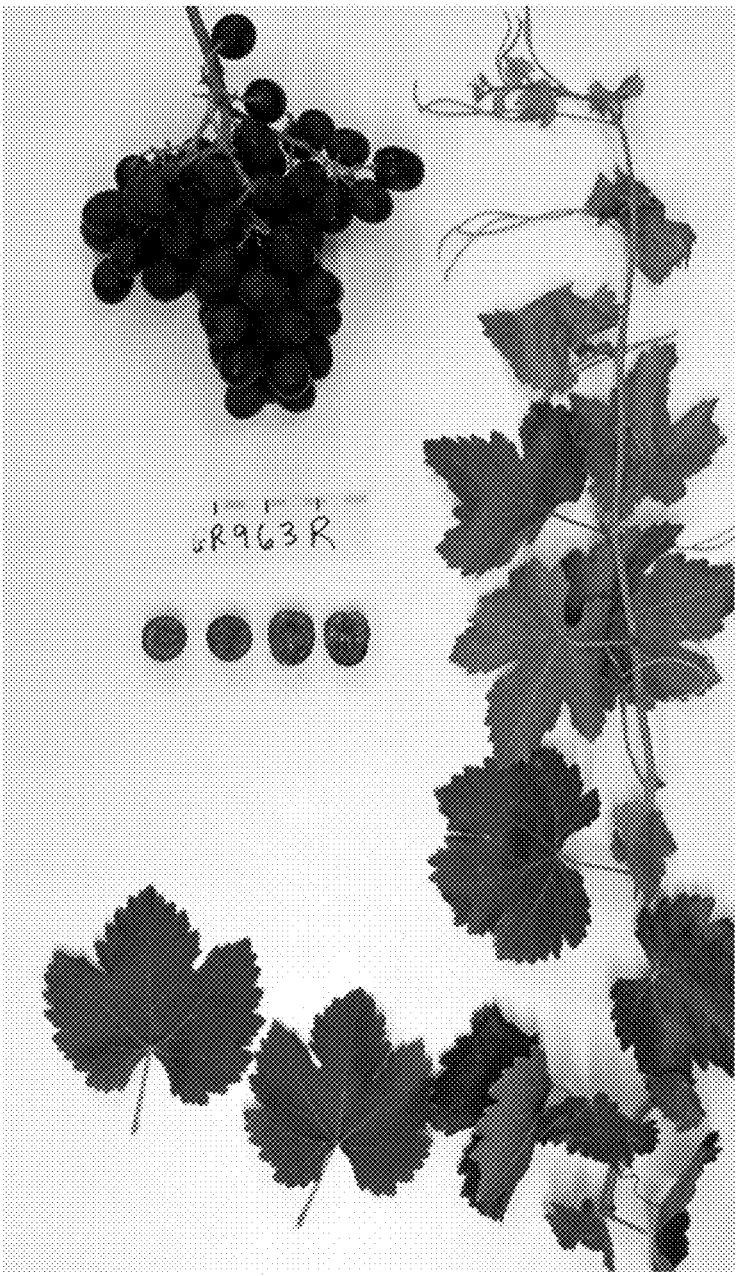
JR963R